United States Patent
Caldeira et al.

(10) Patent No.: US 8,673,219 B2
(45) Date of Patent: Mar. 18, 2014

(54) NASAL PASSAGE INSERTION DEVICE FOR TREATMENT OF RUMINANT EXHALATIONS

(75) Inventors: Kenneth G. Caldeira, Redwood City, CA (US); Roderick A. Hyde, Redmond, WA (US); Muriel Y. Ishikawa, Livermore, CA (US); Jordin T. Kare, Seattle, WA (US); John Latham, Boulder, CO (US); Nathan P. Myhrvold, Bellevue, WA (US); Stephen H. Salter, Edinburgh (GB); Clarence T. Tegreene, Bellevue, WA (US); David B. Tuckerman, Lafayette, CA (US); Thomas Allan Weaver, San Mateo, CA (US); Charles Whitmer, North Bend, WA (US); Lowell L. Wood, Jr., Bellevue, WA (US); Victoria Y. H. Wood, Jr., Livermore, CA (US)

(73) Assignee: Invention Science Fund I, Bellevue, WA (US)

( * ) Notice: Subject to any disclaimer, the term of this patent is extended or adjusted under 35 U.S.C. 154(b) by 206 days.

(21) Appl. No.: 12/927,315

(22) Filed: Nov. 10, 2010

(65) Prior Publication Data

US 2012/0115240 A1    May 10, 2012

(51) Int. Cl.
*G01N 31/10* (2006.01)
*G01N 33/22* (2006.01)

(52) U.S. Cl.
USPC ............. 422/84; 422/88; 422/91; 422/94; 422/95; 422/96; 422/97; 422/98; 436/141

(58) Field of Classification Search
USPC ............. 422/84, 88, 91, 94–98; 436/131, 141
See application file for complete search history.

(56) References Cited

U.S. PATENT DOCUMENTS

| | | | | |
|---|---|---|---|---|
| 2,890,695 | A | * | 6/1959 | Safstrom ................ 128/206.11 |
| 3,457,917 | A | * | 7/1969 | Mercurio ................ 128/204.12 |
| 3,747,597 | A | * | 7/1973 | Olivera .................. 128/206.11 |
| 3,818,899 | A | * | 6/1974 | Venema ........................ 422/84 |
| 3,884,223 | A | * | 5/1975 | Keindl .................... 128/206.11 |
| 3,905,335 | A | * | 9/1975 | Kapp ...................... 128/206.11 |
| 4,009,242 | A | * | 2/1977 | Lauder et al. ............... 423/213.2 |
| 4,042,332 | A | * | 8/1977 | Saitoh et al. .................. 436/175 |
| 4,052,983 | A | * | 10/1977 | Bovender ................ 128/204.12 |
| 4,071,026 | A | * | 1/1978 | Bevins .................... 128/205.29 |
| 4,089,654 | A | * | 5/1978 | Polinski et al. ............... 422/633 |
| 4,126,580 | A | * | 11/1978 | Lauder ............................ 502/303 |
| 4,186,801 | A | * | 2/1980 | Madgavkar et al. .......... 166/256 |
| 4,220,150 | A | * | 9/1980 | King ........................ 128/206.11 |

(Continued)

FOREIGN PATENT DOCUMENTS

| | | |
|---|---|---|
| GB | 2469803 A | 11/2010 |
| JP | 11-137998 | 5/1999 |
| JP | 4014266 B2 | 11/2007 |
| WO | WO 2009/057959 A2 | 5/2009 |

OTHER PUBLICATIONS

Kikuchi, R. et al, Applied Catalysis A: General 2003, 239, 169-179.*
Ciambelli, P. et al, Catalysis Today 2003, 77, 347-358.*

(Continued)

*Primary Examiner* — Arlen Soderquist

(57) ABSTRACT

Methane gas in a ruminant exhalation may be oxidized to reduce the amount of methane gas output by the ruminant.

37 Claims, 9 Drawing Sheets

(56) References Cited

U.S. PATENT DOCUMENTS

| | | | | |
|---|---|---|---|---|
| 4,267,831 A * | 5/1981 | Aguilar | ................... | 128/203.14 |
| 4,327,719 A * | 5/1982 | Childers | ................... | 128/206.11 |
| 4,369,783 A * | 1/1983 | Hiller et al. | ................... | 604/11 |
| 4,788,004 A * | 11/1988 | Pinto et al. | ................... | 252/373 |
| 4,830,844 A * | 5/1989 | Kolts | ................... | 423/437.2 |
| 4,870,025 A * | 9/1989 | Hurley et al. | ................ | 436/141 |
| 4,934,359 A * | 6/1990 | Blaine | ................... | 128/202.16 |
| 4,984,302 A * | 1/1991 | Lincoln | ................... | 2/206 |
| 5,051,241 A * | 9/1991 | Pfefferle | ................... | 422/180 |
| 5,062,423 A * | 11/1991 | Matson et al. | .......... | 128/207.15 |
| 5,117,820 A * | 6/1992 | Robitaille | ................. | 128/206.11 |
| 5,291,897 A * | 3/1994 | Gastrin et al. | ................ | 600/529 |
| 5,326,735 A * | 7/1994 | Itoh et al. | ................... | 502/177 |
| 5,400,797 A * | 3/1995 | Ethridge | ................... | 600/529 |
| 5,417,205 A * | 5/1995 | Wang | ................... | 128/206.11 |
| 5,425,359 A * | 6/1995 | Liou | ................... | 128/206.11 |
| 5,439,865 A * | 8/1995 | Abe et al. | ................... | 502/333 |
| 5,487,268 A * | 1/1996 | Itoh et al. | ................... | 60/274 |
| 5,568,808 A * | 10/1996 | Rimkus | ................... | 128/206.11 |
| 5,580,535 A * | 12/1996 | Hoke et al. | ................. | 423/245.3 |
| 5,648,258 A | 7/1997 | Odom | | |
| 5,665,104 A * | 9/1997 | Lee | ................... | 606/199 |
| 5,666,948 A * | 9/1997 | Matson | ................... | 128/200.23 |
| 5,697,326 A * | 12/1997 | Mottram et al. | ............. | 119/174 |
| 5,804,703 A * | 9/1998 | Wind et al. | ................... | 73/25.01 |
| 5,823,761 A * | 10/1998 | Euzen et al. | ................... | 431/7 |
| 5,843,498 A | 12/1998 | Takahashi | | |
| 5,890,491 A * | 4/1999 | Rimkus | ................... | 128/206.11 |
| 5,972,910 A | 10/1999 | May et al. | | |
| 6,036,950 A | 3/2000 | Baker | | |
| 6,109,262 A * | 8/2000 | Tovey | ................... | 128/206.11 |
| 6,116,014 A * | 9/2000 | Dalla Betta et al. | ............ | 60/777 |
| 6,119,690 A * | 9/2000 | Pantaleo | ................. | 128/206.11 |
| 6,129,680 A * | 10/2000 | Mottram | ................... | 600/532 |
| 6,187,709 B1 | 2/2001 | McCabe | | |
| 6,216,694 B1 * | 4/2001 | Chen | ................... | 128/206.11 |
| 6,309,599 B1 * | 10/2001 | Saint Gal de Pons | ........ | 422/408 |
| 6,393,821 B1 | 5/2002 | Prabhu | | |
| 6,488,635 B1 | 12/2002 | Mottram | | |
| 6,488,907 B1 | 12/2002 | Barnes et al. | | |
| 6,494,205 B1 * | 12/2002 | Brown | ................... | 128/206.11 |
| 6,733,464 B2 * | 5/2004 | Olbrich et al. | ................ | 600/538 |
| 6,962,156 B2 * | 11/2005 | Michaels | ................. | 128/206.11 |
| 6,971,387 B2 * | 12/2005 | Michaels | ................. | 128/206.11 |
| 6,982,161 B1 | 1/2006 | Herrema | | |
| 7,090,873 B2 | 8/2006 | Maye | | |
| 7,156,099 B1 * | 1/2007 | Jenkins | ................... | 128/206.11 |
| 7,214,331 B2 * | 5/2007 | Jiang et al. | ................... | 252/373 |
| 7,247,258 B2 * | 7/2007 | Jung et al. | ................... | 252/373 |
| 7,320,753 B2 | 1/2008 | Roos | | |
| 7,354,467 B2 * | 4/2008 | Chen et al. | ................... | 55/385.1 |
| 7,371,706 B2 | 5/2008 | Ohtsuka et al. | | |
| 7,445,602 B2 * | 11/2008 | Yamamori et al. | ........... | 600/532 |
| 7,524,360 B2 * | 4/2009 | Cheng | ............................ | 95/273 |
| 7,637,983 B1 | 12/2009 | Liu et al. | | |
| 7,745,197 B1 * | 6/2010 | Herrema et al. | ............. | 435/250 |
| 7,841,988 B2 * | 11/2010 | Yamamori | ................... | 600/532 |
| 7,918,225 B2 * | 4/2011 | Dolezal et al. | ............ | 128/206.11 |
| 8,071,342 B2 * | 12/2011 | Herrema et al. | ............. | 435/140 |
| 8,127,767 B2 * | 3/2012 | Mutti et al. | ................. | 128/207.18 |
| 8,177,870 B2 * | 5/2012 | Herrema et al. | ............ | 48/197 R |
| 2003/0086825 A1 * | 5/2003 | Brennan | ................... | 422/83 |
| 2003/0209145 A1 * | 11/2003 | Soper | ................... | 95/273 |
| 2003/0219567 A1 | 11/2003 | Weder | | |
| 2004/0039295 A1 * | 2/2004 | Olbrich et al. | ................ | 600/538 |
| 2004/0065065 A1 * | 4/2004 | Van Patten | .................. | 55/385.1 |
| 2004/0089303 A1 * | 5/2004 | Chien | ................... | 128/206.11 |
| 2004/0192546 A1 | 9/2004 | Dang et al. | | |
| 2004/0261798 A1 * | 12/2004 | Rimkus | ................... | 128/206.11 |
| 2005/0061325 A1 * | 3/2005 | Michaels | ................. | 128/206.11 |
| 2005/0066972 A1 * | 3/2005 | Michaels | ................. | 128/206.11 |
| 2005/0100492 A1 * | 5/2005 | Hoke et al. | ................... | 423/219 |
| 2005/0150008 A1 | 7/2005 | Demmer et al. | | |
| 2005/0199245 A1 * | 9/2005 | Brennan | ................. | 128/207.18 |
| 2006/0057118 A1 | 3/2006 | Toride et al. | | |
| 2006/0204415 A1 * | 9/2006 | Jiang et al. | ................... | 422/211 |
| 2006/0264683 A1 | 11/2006 | Knox et al. | | |
| 2007/0175478 A1 * | 8/2007 | Brunst | ................... | 128/206.18 |
| 2007/0204363 A1 | 8/2007 | Demmer et al. | | |
| 2007/0227542 A1 * | 10/2007 | Kashmakov et al. | ..... | 128/206.11 |
| 2008/0008774 A1 | 1/2008 | Becker et al. | | |
| 2008/0010701 A1 | 1/2008 | Demmer et al. | | |
| 2008/0035151 A1 * | 2/2008 | Solorzano-Garcia | .... | 128/206.11 |
| 2008/0318097 A1 | 12/2008 | Botte | | |
| 2009/0056419 A1 * | 3/2009 | Chang et al. | ................. | 73/31.05 |
| 2009/0101154 A1 * | 4/2009 | Mutti et al. | ............. | 128/207.18 |
| 2009/0126563 A1 | 5/2009 | Caro | | |
| 2009/0288606 A1 | 11/2009 | Zimmerman | | |
| 2010/0085067 A1 * | 4/2010 | Gabriel et al. | ................ | 324/663 |
| 2010/0331777 A1 * | 12/2010 | Danielsson | ................... | 604/104 |
| 2011/0033346 A1 * | 2/2011 | Bohlen et al. | .............. | 422/186.3 |
| 2011/0077544 A1 * | 3/2011 | Abraham-Fuchs et al. | .. | 600/532 |

OTHER PUBLICATIONS

Neumann, D. et al, Catalysis Today 2004, 98, 565-574.*
Persson, K. et al, Journal of Catalysis 2005, 231, 139-150.*
Liotta, L. F. et al, Catalysis Communications 2007, 8, 299-304.*
Beretta, A. et al, Industrial & Engineering Chemistry Research 2009, 48, 3825-3836.*
Atwood et al.; "A crystalline organic substrate absorbs methane under STP conditions"; Chem. Commun.; bearing dates of Nov. 4, 2004, Nov. 11, 2004 and Nov. 30, 2004; pp. 51-53; The Royal Society of Chemistry.
Chagunda et al.; "On the use of a laser methane detector in dairy cows"; Computers and Electronics in Agriculture; Oct. 2009; pp. 157-160 (2 pages—Abstract only); vol. 68; Issue 2; Elsevier B.V.
Cole et al.; "A Review of Bloat in Ruminants"; Journal of Animal Science; bearing a download date of Apr. 18, 2010 and publication year 1945; pp. 183-236; vol. 4; American Society of Animal Science.
Corro et al.; "A study of Pt-Pd/y- Al2 O3 catalysts for methane oxidation resistant to deactivation by sulfur poisoning"; Journal of Molecular Catalysis A: Chemical; Jan. 2, 2010; pp. 35-42 (3 pages—Abstract only); vol. 315; Issue 1; Elsevier B.V.
Crabtree, Robert; "Aspects of Methane Chemistry"; Chemical Reviews 1995; bearing dates of Jun. 29, 1994 and Mar. 21, 1995; pp. 987-1007; vol. 95; No. 4; American Chemical Society.
Deng et al.; "Oscillations of methane combustion over alumina-supported palladium catalysts under oxygen-deficient conditions"; Journal of Molecular Catalysis A: Chemical; bearing dates of Feb. 12, 2998 and Aug. 4, 1998; pp. 51-60; vol. 142; Elsevier Science B.V.
Dos Santos Rodrigues et al.; "Analysis of Methane Biodegradation by Methylosinus trichosporium OB 3b"; Brazilian Journal of Microbiology; bearing dates of Jun. 11, 2008, Sep. 4, 2008 and Mar. 31, 2009; pp. 301-307; vol. 40.
Farminfo.org; "Nutrient Requirements"; located at http://www.farminfo.org/beef/nutrient.htm; printed on Oct. 29, 2010; 19 pages total.
Gelin et al.; "Complete oxidation of methane at low temperature over noble metal based catalysts: a review"; Applied Catalysis B: Environmental; bearing dates of Oct. 29, 2001, Mar. 20, 2002 and Mar. 25, 2002; pp. 1-37; vol. 39; Elsevier Science B.V.
Graetzel et al.; "Methane oxidation at room temperature and atmospheric pressure activated by light via polytungstate dispersed on titania"; J. Phys. Chem.; bearing dates of May 1989 and Feb. 12, 2010; pp. 4128-4132 (Abstact only—2 pages); vol. 93; No. 10; American Chemical Society.
Guo et al.; "Avoiding Loss of Catalytic Activity of Pd Nanoparticles Partially Embedded in Nanoditches in SiC Nanowires"; Nanoscale Res. Lett.; bearing dates of Sep. 28, 2009, Oct. 28, 2009 and Nov. 15, 2009; pp. 332-337; vol. 5; Springer.
Huang, Guangyu; "Catalytic Combustion of Lean Methane on Commerical Palladium-Based Catalysts"; Thesis Submitted to the Faculty of Graduate Studies and Research at the University of Alberta; Spring 2010; pp. 1-112 + table of contents, cover sheet, etc; Guangyu Huang.
Huffman, C.F.; "The Mysteries of the Rumen[1]"; Journal of Dairy Science 50th Anniversary Issue; printed on Oct. 20, 2010; pp. 688-692; Dairy Department, Michigan State University, East Lansing, MI.

(56) References Cited

OTHER PUBLICATIONS

Ishler, Virginia; "Carbon, methane emissions and the dairy cow"; Penn State College of Agricultural Sciences Nutrient Management; printed on Oct. 20, 2010; pp. 1-4 + cover pages (2); Pennsylvania State University, University Park, PA.

Johnson et al.; "Methane emissions from cattle"; Journal of Animal Science; bearing dates of 1995 and Oct. 11, 2009; pp. 2483-2492; vol. 73; American Society of Animal Science.

Kleiber et al.; "Bloat in Cattle and Composition of Rumen Gases"; bearing a date of Feb. 20, 1943; pp. 929-933; College of Agriculture, University of California, Davis, CA.

Krishna. et al.; "Sunlight-assisted photocatalytic oxidation of methane over uranyl-anchored MCM-41"; Catalysis Letters; Nov. 2004; pp. 113-116; vol. 98; Nos. 2-3; Plenum Publishing Corporation.

Li et al.; "A Review on Complete Oxidation of Methane at Low Temperatures"; Journal of Natural Gas Chemistry; bearing dates of Jun. 3, 2003 and Aug. 8, 2003; pp. 153-160; vol. 12; No. 3; Science Press.

Lien et al.; "Photooxidation of Methane over $TiO_2$"; Journal of the Chinese Chemical Society; 2004; pp. 37-42; vol. 51; No. 1.

Los Angeles Times; "World—Graphic: From the farm"; bearing a date of Jun. 7, 2008; p. 1; located at http://www.latimes.com/news/nationworld/world/la-060708-fg-burp-g,0,731431.graphic; LATimes.com.

Majak et al.; "Bloat in Cattle"; Agriculture and Agri-Food Canada; bearing dates of May 2003 and Apr. 2008; pp. 1-28 + cover sheet, table of contents, etc.; Alberta Agriculture and Rural Development; Edmonton, Alberta Canada.

Mallett et al.; "Progress in Developing Ventilation Air Methane Mitigation and Utilisation Technologies"; printed Nov. 4, 2010; pp. 1-18; CSIRO Exploration and Mining, Technology Court, Pullevale, Australia.

Mitloehner et al.; "Direct measurements improve estimates of dairy greenhouse-gas emissions"; California Agriculture; Apr.-Jun. 2009; pp. 79-83; vol. 63; No. 2.

Neate, Rupert; "Cow farts collected in plastic tank for global warming study"; located at http://www.telegraph.co.uk/news/newstopics/howaboutthat/2274995; Jul. 9, 2008; pp. 1-2; Telegraph Media Group Limited 2010.

On et al.; "New SO2 resistant mesoporous La-Co-Zr mixed oxide catalysts for hydrocarbon oxidation"; Phys. Chem. Chem. Phys.; bearing dates of Mar. 17, 2003, Apr. 24, 2003 and May 13, 2003; pp. 2724-2729; vol. 5; The Owner Societies 2003.

Ordonez et al.; "Methane catalytic combustion over Pd/Al2 O3 in presence of sulphur dioxide: development of a regeneration procedure"; Catalysis Letters; Mar. 2005; p. 27 only; vol. 100; Nos. 1-2; Springer Science-Business Media, Inc.

Physorg.Com; "Cow Backpacks Trap Methane Gas"; located at http://www.physorg. Com/news135003243.html; bearing a date of Jul. 22, 2008 and printed on Nov. 10, 2010; p. 1.

Ramirez-Lopez et al.; "Complete Oxidation of Methane Over Pt/CeO2-Al2O3 Catalysts"; Chem. Eng. Comm.; bearing dates of 2009 and Feb. 14, 2010; pp. 1189-1197; vol. 196; Taylor & Francis Group, LLC.

Steinfeld et al.; "Livestock's role in climate change and air pollution (Chapter 03)"; Livestock's Long Shadow environmental issues and options; Food and Agriculture Organization of the United Nations—Rome 2006; bearing a date of 2006; pp. 79-123 + cover page; The Livestock, Environment and Development (LEAD) Initiative.

Su et al.; "Catalytic combustion of coal mine ventilation air methane"; Fuel; bearing dates of Aug. 22, 2005, Nov. 22, 2005, and Dec. 20, 2005; pp. 1201-1210; vol. 85; Elsevier Ltd.

Tompos et al.; "Characterization of Trimetallic Pt-Pd-Au/$CeO_2$ Catalysts Combinatorial Designed for Methane Total Oxidation"; Combinatorial Chemistry & High Throughput Screening; 2007; pp. 71-82; vol. 10; No. 1; Bentham Science Publishers Ltd.

United Nations Framework Convention on Climate Change; "Ireland's Fifth National Communication"; printed on Nov. 4, 2010; pp. 1-139.

US Environmental Protection Agency Coalbed Methane Outreach Program; Global Overview of CMM Opportunities; Jan. 2009; pp. 1-260 + 32 addit pages comprised of the cover sheet, acknowledgment and contents pages.

Walther et al.; "Low temperature methane oxidation on differently supported 2 nm Au nanoparticles"; Gold Bulletin; 2009; pp. 13-19; vol. 42; No. 1.

Watson, Paul; "New Zealand aims for greener pastures"; Los Angeles Times—Article Collections; http://articles.latimes.com/2008/jun/08/world/fg-burp8; bearing a date of Jun. 8, 2008 and printed on Oct. 29, 2010; pp. 1-3; Los Angeles Times.

Wikipedia; "Methane"; bearing dates of Oct. 26, 2010 and Oct. 29, 2010; pp. 1-10; Wikipedia.org.

Xiao et al.; "Catalytic Combustion of Methane over CeO2-MOx (M=La3+, Ca2+) Solid Solution Promoted Pd/y-Al2O3 Catalysts"; Acta Physico-Chimica Sinica; Nov. 2008; pp. 2108-2113; vol. 24; Issue 11; Elsevier B.V.

Xiao et al.; "Low-temperature catalytic combustion of methane over Pd/CeO2 prepared by deposition-precipitation method"; Catalysis Communications; bearing dates of Jan. 29, 2005, Jul. 22, 2005 and Sep. 19, 2005; pp. 796-801; vol. 6; Elsevier B.V.

Zhang et al.; "Carbon Nanotubes as Active Components for Gas Sensors"; Journal of Sensors; bearing dates of Dec. 24, 2008, Mar. 30, 2009 and Apr. 13, 2009; pp. 1-16; vol. 2009; Article ID: 160698; Hindawi Publishing Corporation.

Zhao et al.; "Hydrogen-atom abstraction from methane by stoichiometric early transition metal oxide cluster cations"; Chem. Commun.; bearing a date of Mar. 29, 2010 and 2010; pp. 1736-1738 (1 page—Abstract only); vol. 46; Royal Society of Chemistry 2010.

\* cited by examiner

NASAL PASSAGE INSERTION DEVICE FOR TREATMENT OF RUMINANT EXHALATIONS

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

In one embodiment, an apparatus comprises a device suitable for retention in a nasal passage of a ruminant, the device being arranged to pass a ruminant exhalation, the device including a first structure configured to oxidize methane gas in the ruminant exhalation, the device being further arranged to pass products of the oxidized methane gas toward a nasal passage exit.

In one embodiment, a method comprises receiving a ruminant exhalation in a first region of the nasal passage of a ruminant, and oxidizing methane gas in the ruminant exhalation at least partially within the first region of the nasal passage of the ruminant.

In one embodiment, a method comprises: receiving a first input signal corresponding to a first measurement of a ruminant exhalation, the first measurement corresponding to an un-oxidized portion of the ruminant exhalation; receiving a second input signal corresponding to a second measurement of a ruminant exhalation, the second measurement corresponding to an oxidized portion of the ruminant exhalation; and producing a first output signal based on a difference between the first input signal and the second input signal.

In one embodiment, a method comprises: receiving a first input signal corresponding to a difference between a first measurement of a ruminant exhalation obtained prior to oxidation of the exhalation and a second measurement of a ruminant exhalation obtained after oxidation of the exhalation; and producing a first output signal based on the received first input signal and corresponding to an amount of methane oxidized in the oxidation of the exhalation.

In one embodiment, a method comprises: receiving a first input signal corresponding to a first measurement of a ruminant exhalation obtained after oxidation, within a nasal passage of the ruminant, of the exhalation; and producing a first output signal based on the received first input signal and corresponding to an amount of methane oxidized in the oxidation of the exhalation.

In one embodiment, a method comprises detecting a post-oxidation level of methane exiting a ruminant; and responsive to the detecting, producing an indicator of the post-oxidation level.

In one embodiment, an apparatus comprises: circuitry configured to receive a first input signal corresponding to a first measurement of a ruminant exhalation, the first measurement corresponding to an un-oxidized portion of the ruminant exhalation; circuitry configured to receive a second input signal corresponding to a second measurement of a ruminant exhalation, the second measurement corresponding to an oxidized portion of the ruminant exhalation; and circuitry configured to produce a first output signal based on a difference between the first input signal and the second input signal.

In one embodiment, an apparatus comprises: circuitry configured to receive a first input signal corresponding to a difference between a first measurement of a ruminant exhalation obtained prior to oxidation of the exhalation and a second measurement of a ruminant exhalation obtained after oxidation of the exhalation; and circuitry configured to produce a first output signal based on a the received first input signal and corresponding to an amount of methane oxidized in the oxidation of the exhalation.

In one embodiment, an apparatus comprises: circuitry configured to receive a first input signal corresponding to a first measurement of a ruminant exhalation obtained after oxidation, within a nasal passage of the ruminant, of the exhalation; and circuitry configured to produce a first output signal based on the received first input signal and corresponding to an amount of methane oxidized in the oxidation of the exhalation.

In one embodiment, an apparatus comprises a device attachable to the nasal septum of a ruminant and a first structure supported by the device and arranged to oxidize methane gas in an exhalation of the ruminant.

DETAILED DESCRIPTION

Figure 1:
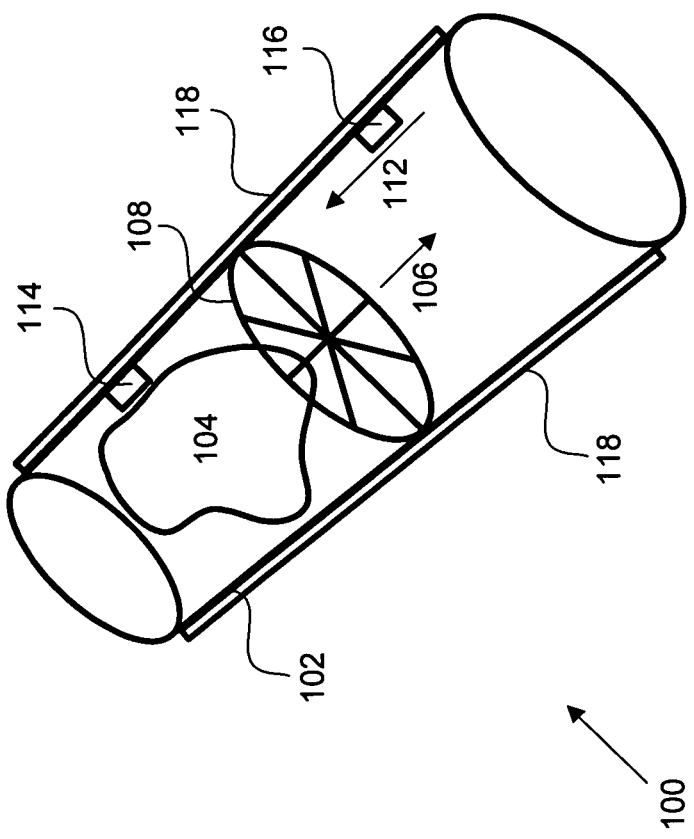
FIG. 1 shows a device suitable for insertion into the nasal passage of a ruminant.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Catalytic converters are used to reduce pollution from vehicle emissions. A configuration similar to that of a catalytic converter for a vehicle may be used to reduce emissions of certain gasses such as methane ($CH_4$) from an animal.

FIG. 1 shows an embodiment of an apparatus 100 comprising a device 102 suitable for retention in or attachable to a nasal passage of a ruminant, the device 102 being arranged to pass a ruminant exhalation 104, the device 102 including a first structure 108 configured to oxidize methane gas in the ruminant exhalation 104, the device 102 being further arranged to pass products of the oxidized methane gas toward a nasal passage exit in a direction 106. The ruminant may be a cow, a sheep, a goat, or a different animal.

As the ruminant exhalation 104 travels through the device 102 in the direction 106, the first structure 108 may be configured to oxidize methane gas in the ruminant exhalation 104. The device 102 may be configured such that when the animal is inhaling and gasses are flowing in the direction 112, the animal may breathe normally.

The first structure 108 is shown in FIG. 1 as having substantially 2D radial symmetry. However, the composition of the first structure 108 may be selected to maximize the exposure of the ruminant exhalation 104 to the surface area of the first structure 108. For example, the first structure 108 may include a substantially 3D honeycomb structure, wherein the cell size of the honeycomb may be selected to maximize the surface area of the first structure 108, while still allowing passage of the ruminant exhalation 104. Or, the first structure 108 may include a substantially spiral coil. While a honeycomb and spiral coil are given as two examples of the composition of the first structure 108, the first structure may take a variety of forms, including a rectilinear geometry, a substantially random geometry, or a different geometry selected according to the application.

The first structure 108 may be formed from a variety of materials. For example, in some embodiments the first structure may be formed from a catalyst selected to oxidize methane gas, including but not limited to a noble metal (such as palladium, platinum, gold, and/or a different noble metal), a rare earth element, a metal oxide, a transition metal, and/or a different catalyst or material. In some embodiments, the first structure may be formed from a substrate such as a ceramic and/or a metal and may be coated with a material selected to oxidize methane gas. In an embodiment, which will be described in greater detail with respect to FIG. 3, the first structure 108 may include a first substrate, a first washcoat support, and a first catalyst carried by the washcoat support.

In some embodiments the first structure 108 may be heated, wherein the first structure 108 may oxidize methane gas with greater efficiency in a selected temperature range, which will be described in greater detail with respect to FIG. 4.

The apparatus may further comprise a first detector 114 supported by the device 102 and arranged to detect a substance such as methane, a methane oxidation product (such as carbon monoxide, carbon dioxide, water, or a different product), or a different substance proximate to a first location on the device 102. For example, the detector 114 may be configured to detect an amount of the substance in a region, a threshold level of the substance, or it may detect the substance in a different way. The first location may be selected such that the detector 114 is arranged to detect a substance in an unoxidized portion of the ruminant exhalation. For example, it may simply detect in a region that is upstream (specifically, upstream during exhalation) from the first structure 108 or otherwise detect the substance in the ruminant exhalation 104 prior to oxidation of the exhalation.

The first location may be selected such that the first detector 114 is arranged to detect a substance in a portion of the ruminant exhalation that bypasses the first structure 108. For example, FIG. 1 shows the first structure 108 as having a cross-section that substantially spans the width of the device 102. However, in some embodiments the first structure 108 may occupy only a fraction of the width of the device, such that a portion of the ruminant exhalation 104 may pass through the device 102 without being oxidized. In this case, a first detector 114 may be arranged to detect the amount of a substance in the portion of the ruminant exhalation 104 that bypasses the first structure 108. Another way this may occur is in an embodiment where the device 102 includes more than one channel, where in this embodiment one or more channels may be configured without a first structure 108 such that the portion of the ruminant exhalation that passes through these channels remains un-oxidized, and a detector such as the first detector 114 may be placed in one or more channels not having a first structure 108, in order to detect a substance in the un-oxidized portion of the ruminant exhalation. In some embodiments the device 102 may include at least two different channels having one-way valves such that one channel is configured to pass the ruminant exhalation in the direction 106 and one channel is configured to pass ambient air in the direction 112; in such an embodiment the first structure 108 could be situated such that ambient air passing in the direction 112 would not pass through and be heated by the first structure 108. In such an embodiment the valves could be actively controlled dependent on a detected level of methane and/or methane oxidation product.

The apparatus may further comprise a second detector 116 supported by the device 102 and arranged to detect a substance such as methane, a methane oxidation product (such as carbon monoxide, carbon dioxide, water, or a different product), or a different substance proximate to a second location on the device 102, the second location being different from the first location. Similarly to the first detector 114, a detector 116 may be configured to detect an amount of the substance in a region, a threshold level of the substance, or it may detect the substance in a different way. The first and second detectors 114, 116 may be configured to detect the same substance, different substances, or in some embodiments they may each be configured to detect a multitude of substances, in which case the substances they are configured to detect may be the same, different, or partially overlapping.

The first and second detectors 114, 116 may be any kind of detector configured to detect a gas. For example, they may include one or more spectroscopic detectors (which may include, for example, a laser or other source of electromagnetic energy), one or more detectors including a carbon nanotube (as described in, "CARBON NANOTUBES AS ACTIVE COMPONENTS FOR GAS DETECTORS", Wei-De Zhang et al., Journal of Sensors, Volume 2009, Article 160698, which is incorporated herein by reference), and/or a different kind of detector.

In some embodiments, the first structure 108 may have an on state and an off state. For example, the first structure 108 may oxidize methane gas optimally in a first temperature range $\Delta T_1$ and the first structure 108 may be considered to be in an on state while it is within the first temperature range $\Delta T_1$. Similarly, the first structure 108 may provide little or no oxidation of methane gas in a second temperature range $\Delta T_2$, and the first structure 108 may be considered to be in an off state while it is within the second temperature range $\Delta T_2$. Thus, the first and second detectors 114, 116 may be configured such that one detects an amount of substance in the ruminant exhalation 104 when the first structure 108 is in the on state, and the other detects an amount of substance in the ruminant exhalation 104 when the first structure 108 is in an off state. Further, there may be more than two detectors, and the detectors may be configured in such a way as to provide the desired measurements according to a particular embodiment.

The detectors 114, 116 may be positioned such that the first detector 114 is upstream (specifically, upstream during exhalation) from the first structure 108 and the second detector 116 is downstream (specifically, downstream during exhalation) from the first structure 108, as is shown in FIG. 1. However, other configurations of detectors may be desirable based on a particular embodiment.

The apparatus 100 may further comprise an insulator 118 arranged to thermally insulate at least a portion of the device 102 from the nasal passage of the ruminant. Although the insulator 118 is shown as being integral to the device 102 in FIG. 1, in some embodiments it may be completely or partially separate. For example, the insulator 118 may in some embodiments be a separate element that may fit in the nasal passage of the ruminant, wherein the device 102 may be configured to fit inside the insulator 118. In another embodiment, the insulator may comprise two separate pieces, such as a first piece that fits in the nasal passage of the ruminant, and a second piece that lines the outside of the device 102, wherein the device 102 may be configured to fit inside the first piece of the insulator. There are many ways in which the insulator may be configured relative to the device 102, and one skilled in the art may adapt the design according to a particular embodiment.

The apparatus 100 may further include one or more springs or other mechanical devices configured to hold the apparatus 100 in place in the nasal passage of the ruminant. In some embodiments the size of the apparatus 100 may be selected such that no such springs or other mechanical devices are necessary for holding the apparatus 100 in place. In some embodiments the apparatus 100 may be at least partially enveloped in a material configured to expand responsive to moisture to hold the apparatus 100 in place.

Figure 2:
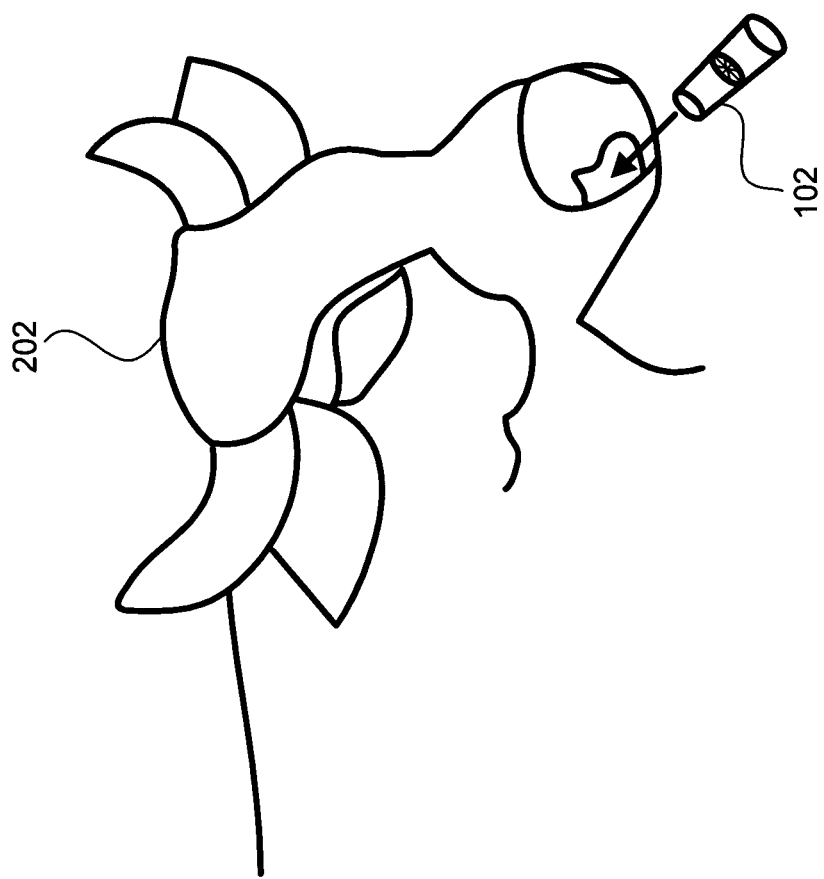
FIG. 2 shows the device of FIG. 1 and a cow.

The device 102 is shown relative to a ruminant 202 in FIG. 2, where in this embodiment the ruminant is a cow. Although only one device 102 is shown, in some embodiments a device 102 may be fitted to each of the animal's nostrils.

Although the device 102 is shown in FIG. 2 as being configured to fit inside the nasal passage of the ruminant, in other embodiments the device 102 may be configured in a different way. For example, in some embodiments the device 102 may be attachable to the nasal septum of a ruminant, similar to the nose ring of a cow. In such an embodiment, the device 102 may be configured similarly to the embodiment shown in FIG. 1. In other embodiments, a device may be attachable to the nasal septum of a ruminant and be configured to ignite in the presence of methane gas.

Figure 3:
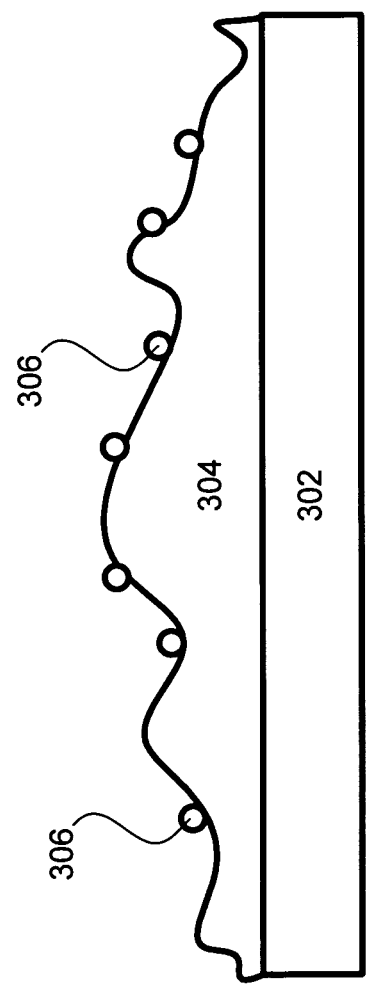
FIG. 3 shows a substrate, a washcoat support, and a catalyst.

In one embodiment the first structure 108 configured to oxidize methane gas includes a first substrate 302, a first washcoat support 304 in intimate contact with the first substrate 302, and a first catalyst 306 (such as a noble metal) carried by the first washcoat support 304. The substrate 302 may include, for example, a ceramic, a metal, and/or a different material. The first washcoat support 304 may include alumina, silica, and/or a different material. The first catalyst 306 may include palladium (Pd), platinum (Pt), gold (Au), rhodium (Rh), iridium (Ir), combinations thereof, and/or a different material. In some embodiments the first substrate 302 may form a substantially honeycomb structure, wherein the honeycomb structure may have, for example, a density between 10-100 cells/cm, however the first substrate 302 may form a variety of different configurations. Different configurations of the first structure 108 (where the configuration of the substrate 302 may be substantially equivalent to the configuration of the first structure 108) have been described with respect to FIG. 1. Examples of the type of configuration of FIG. 3 are described in U.S. Patent Application No. 2004/0192546 to Dang et al., entitled CATALYST FOR THE LOW TEMPERATURE OXIDATION OF METHANE, which is incorporated herein by reference, and in U.S. Pat. No. 5,741,467 to Burton et al., entitled PALLADIUM CATALYST WASHCOAT SUPPORTS FOR IMPROVED METHANE OXIDATION IN NATURAL GAS AUTOMOTIVE EMITION CATALYSTS, which is incorporated herein by reference.

Although FIG. 3 shows the catalyst 306 as being small particles, this is for illustrative purposes only, and there are other ways that the catalyst 306 may be distributed on the washcoat support 304. For example, the catalyst 306 may form a substantially thin film on the washcoat support 304, may be distributed throughout the washcoat support 304 instead of just on the surface, and/or may be distributed in a different way.

Figure 4:
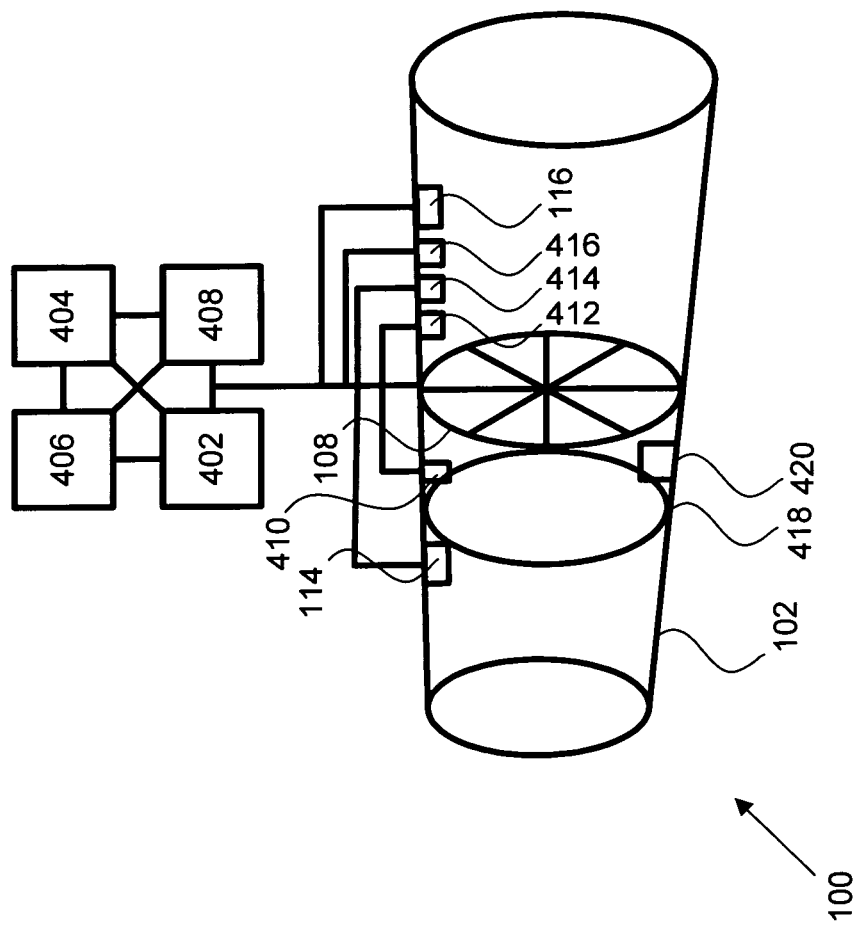
FIG. 4 shows a device suitable for insertion into the nasal passage of a ruminant with other elements of an apparatus.

The apparatus 100 may further comprise circuitry 402, shown in FIG. 4, operably connected to the first structure 108 to control the oxidation of the methane gas. In some embodiments, the circuitry 402 may be configured to receive a signal from the first and second detectors 114, 116, and may further be configured to determine a difference between the signal from the first detector 114 and the signal from the second detector 116. The apparatus 100 may further comprise a storage medium 404. The storage medium 404 may be operably connected to the circuitry 402, wherein the storage medium 404 may be configured to store the signals from the first and second detectors 114, 116, and/or it may be configured to store the determined difference between the signal from the first detector 114 and the signal from the second detector 116. The storage medium may include one or more mechanisms by which a user may retrieve information from it, including but not limited to an RFID, a removable disk, and/or another mechanism. In some embodiments the circuitry 402 may be further configured to determine an amount of methane oxidized based on the received signals from the first and second methane detectors 114, 116. The apparatus 100 may further comprise a transmitter 406, wherein the transmitter 406 may be operably connected to the circuitry 402, the transmitter 406 being configured to send the signals from the first and second detectors 114, 116, and/or it may be configured to send a first signal corresponding to the determined amount of methane oxidized.

In some embodiments the device 102 may be associated with an identification, wherein the identification may correspond to the ruminant 202, the device 102, the location of the ruminant 202, and/or an entity associated with the ruminant 202 (such as a farm that owns the cow, a field or building number within the farm, or another entity that may be associated with and/or identify the ruminant). The identification may be a name, a number, or a different identifier. The identification may be included with information sent, received, stored, or otherwise used in relation to the device 102. For example, with reference to FIG. 4, the circuitry may be configured to receive and/or send the identification along with other signals related to the ruminant 202. Similarly, the storage medium 404 may be configured to store the identification along with other information related to the ruminant, in particular, information related to the oxidation of methane.

The apparatus may further comprise a tracker 412 configured to determine the location of the ruminant. The tracker 412 may include, for example, a GPS receiver and/or a different device for determining the location of the ruminant. The tracker 412 may be configured to produce the identification as described previously, and/or may be operably connected to one or more of the elements corresponding to the device 102, such as the circuitry 402, the storage medium 404, the transmitter 406, and/or another element, wherein the elements may be configured to send and/or receive information produced by the tracker 412.

In some embodiments the circuitry 402 may be configured to determine an amount of methane oxidized by the device 102. For example, in one embodiment the first detector 114 may be configured to determine an amount of methane in the un-oxidized ruminant exhalation (examples of measurements of the un-oxidized ruminant exhalation have been described with respect to FIG. 1), and the second detector 116 may be configured to determine an amount of methane in the ruminant exhalation after the oxidation. The first and second detectors 114, 116 may send signals to the circuitry 402, and the circuitry 402 may determine the amount of methane oxidized by determining a difference between the detected amounts of methane.

In some embodiments, only one measurement may be used to determine the amount of methane oxidized. For example, the amount of methane in the un-oxidized ruminant exhalation may be pre-determined, and the circuitry 402 may only receive a signal indicating the amount of methane in the oxidized ruminant exhalation.

In some embodiments, the circuitry 402 may be further configured to determine an amount of a methane oxidation product produced by the methane oxidations such as carbon monoxide, carbon dioxide, water, or a different product. This may be deduced according to the amount of methane oxidized or it may be measured directly, wherein the measurement may be similar to those previously described for methane oxidation. Further, in some embodiments the amount of methane oxidized may be determined according to measurements of a methane oxidation product. For example, where the first and second detectors 114, 116 are configured to detect carbon dioxide, the circuitry 402 may be configured to infer an amount of methane oxidized based on the amount of carbon dioxide produced.

In some embodiments the circuitry 402 may be further configured to determine a time interval associated with the amount of methane oxidized. For example, the first and second detectors 114, 116 may be configured to send one or more signals corresponding to the time and/or time duration at/during which a measurement was obtained, wherein the circuitry may determine a corresponding time and/or time interval associated with a measurement corresponding to methane oxidation. Or, the circuitry may be configured with a clock and may be further configured to determine the time at which a signal is received (for example, from the first and/or second detectors 114, 116) and/or to determine a time duration during which a measurement was performed. There are many ways in which the circuitry 402, detectors 114, 116, and/or other elements may be configured in order to determine and/or associate a time and/or time duration of a measurement, and one skilled in the art may adapt the configuration to a particular embodiment.

The apparatus may further comprise a heating element 410 arranged to heat the first structure, where the heating element may be an electrical resistance heater or other type of heater, and may further comprise circuitry 402 arranged to control the heating element 410 and/or a power supply 408 arranged to provide power to the heating element 410. In some embodiments the power supply 408 may include a battery, wherein the battery may be rechargeable. In some embodiments the power supply 408 may be further configured to receive energy from the ruminant exhalation. In some embodiments the power supply 408 may be configured to be mounted at a location different from the device 102, such as on the ruminant or in a different location.

The apparatus may further comprise a heat sensor 414 arranged to measure a temperature proximate to the first structure and/or a fan 420 arranged to transfer heat away from the device 102. Although a fan 420 is shown in FIG. 4 as the device configured to transfer heat away from the device 102, in other embodiments this may be accomplished by one or more heat pipes or other devices. In some embodiments, the heating element 410, the heat sensor 414, the fan 420, and the circuitry 402 may be incorporated together such that the first structure 108 is configured to heat to a certain temperature, wherein the heating element 410 may automatically turn off when the first structure 108 reaches the desired temperature. Further, the fan 420 may be configured to turn on automatically if the first structure 108 exceeds a certain temperature. In some embodiments, the fan 420 may be configured to be on during a substantial percentage of time when the device 102 is in use. The fan 420 may be used to expel the ruminant exhalation 104 from the device with a greater force than would occur without the fan, and/or may otherwise be used to regulate the flow of the ruminant exhalation 104 through the device.

In some embodiments, heat regulation of the first structure 108 (via the heating element 410, the fan 420; monitored via the heat sensor 414; and/or including one or more other elements conducive to heat regulation of the device) may be responsive to the methane oxidation by the device. For example, the oxidation of the methane may be monitored by detectors 114, 116, and the circuitry 402 may be configured to determine absolute or relative rates of methane oxidation. The rates of methane oxidation may then be altered by altering the temperature of the first structure 108, wherein the process may be automated via the circuitry 402, and/or may receive user input to aid in determining changes in temperature. These changes may, in some embodiments, be performed iteratively, i.e.: change temperature; determine new rate of methane oxidation; change temperature again based on new rate of methane oxidation, and etc. until the desired rate of methane oxidation is achieved.

In some embodiments, heat regulation of the first structure 108 may be responsive to the detection of methane or another substance in the ruminant exhalation 104. For example, the detector 114 may be positioned upstream (specifically, upstream during exhalation) of the first structure 108 and may be configured to detect a threshold level of methane in the ruminant exhalation 104, wherein the circuitry 402 may be responsive to the positive detection of the threshold level of methane to heat the first structure 108 (via the elements as described above) such that it may oxidize the methane in the ruminant exhalation.

Methane oxidation rates may further be controlled by a shutter or flow control device 418, which may be configured to adjust the flow of the ruminant exhalation through the first structure 108 and/or to adjust the exposure of the first structure 108 to the ruminant exhalation 104. The shutter or flow control device 418 may be operably connected to the circuitry 402 as described previously for the elements conducive to heat regulation, wherein the circuitry may change the flow of the ruminant exhalation 104 through the first structure 108 according to the rate of methane oxidation.

In some embodiments, the heat sensor 414 may be configured to determine temperature proximate to the device 102, and the apparatus 100 may further comprise a meter 416 configured to determine a volume of ruminant exhalation expelled through the nasal passage of the ruminant, and the circuitry 402 may be configured to determine an amount of methane oxidized based on the determined temperature and volume of ruminant exhalation expelled.

Although the circuitry 402 is shown in FIG. 4 as a single unit, in different embodiments the circuitry 402 may include several different units, where the different units may have the same, different, or similar functions. For example, in one embodiment one unit of circuitry may be incorporated with and operably connected to the detectors 114, 116, while a separate unit of circuitry may be incorporated with and operably connected to the heating element 410. Other embodiments may include more than two units of circuitry. There are many ways of incorporating the circuitry in a system and one skilled in the art may arrange the circuitry 402 according to a particular application.

One or more of the elements as shown and described with respect to FIGS. 1-4 may be configured to send one or more signals, to other elements of the apparatus 100 and/or to one or more locations different from the apparatus. For example, as described previously, the circuitry 402 may be configured to send and/or receive one or more signals from the storage medium 404. Further, the circuitry 402 and/or the storage medium 404 may be configured to send one or more signals to one or more locations separate from the apparatus, such as a central processor configured to receive signals from many ruminants outfitted with the apparatus 100 in a certain geographical area. The signals may be sent electronically, wirelessly, optically such as via an optical fiber, and/or in another way. There are many ways of configuring the apparatus 100 such that the elements of the apparatus 100 may transmit signals to each other and/or to one or more locations external to the apparatus, and one skilled in the art may adapt the mode of transmission of signals according to their particular application.

Although some of the elements of FIG. 4 are shown as being integral to the device 102 (such as the tracker 412, meter 416, etc.) and some elements are shown as being substantially outside the device (such as the circuitry 402, storage medium 404, etc.), whether an element is incorporated within the device 102 or external to and/or separate from the device 102 may depend on the application and factors such as the size of the element, benefits from proximity of different elements, etc.

Although FIG. 4 includes many elements, some embodiments may not include all of the elements as shown. For example, in a very simple embodiment, the device 102 may include the first structure 108 and the heating element 410, where the heating element may be configured to heat the first structure 108. In this embodiment, the heating element 410 may be configured to heat to a certain temperature and/or may include circuitry 402 configured to control the heating element 410.

Figure 5:
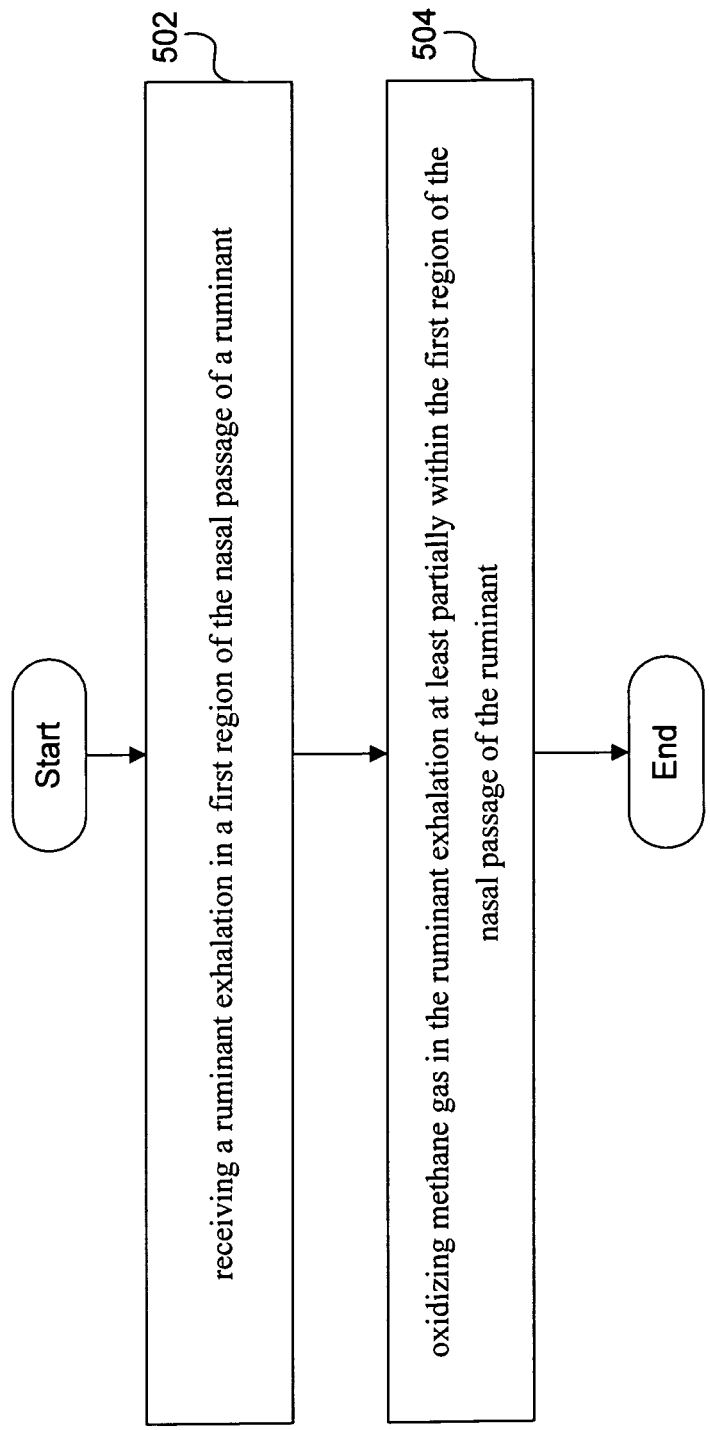
FIGS. 5-9 are each flow charts illustrative of a method.

In one embodiment, depicted in the flow chart of FIG. 5 (wherein the method may be performed with the apparatus 100 as described with respect to FIGS. 1-4), a method comprises (502) receiving a ruminant exhalation in a first region of the nasal passage of a ruminant (wherein the first region may include at least a portion of a region of the first structure 108), and (504) oxidizing methane gas in the ruminant exhalation at least partially within the first region of the nasal passage of the ruminant.

In some embodiments, the method may further comprise detecting the presence of a first methane oxidation product in an un-oxidized portion of the ruminant exhalation, and may further comprise sending a signal corresponding to the detected presence of the first methane oxidation product in an un-oxidized portion of the ruminant exhalation. In some embodiments, detecting the presence of a first methane oxidation product in an un-oxidized portion of the ruminant exhalation may include detecting the presence of the first methane oxidation product in the ruminant exhalation prior to oxidizing the methane in the ruminant exhalation.

The method may further comprise detecting the presence of the first methane oxidation product in the ruminant exhalation after oxidizing the methane in the ruminant exhalation, and sending a signal, the signal corresponding to the detected presence of the first methane oxidation product in the ruminant exhalation after oxidizing the methane in the ruminant exhalation.

The method may further comprise determining a difference between the detected amount of the first methane oxidation product in the un-oxidized portion of the ruminant exhalation and the detected amount of the first methane oxidation product in the ruminant exhalation after oxidizing the methane in the ruminant exhalation. The method may further comprise determining an amount of methane oxidized based on the determined difference between the detected amount of the first methane oxidation product in the un-oxidized portion of the ruminant exhalation to the detected amount of the first methane oxidation product in the ruminant exhalation after oxidizing the methane in the ruminant exhalation. The method may further comprise determining an amount of a second methane oxidation product produced based on the determined difference between the detected amount of the first methane oxidation product in the ruminant exhalation prior to oxidizing the methane in the ruminant exhalation to the detected amount of the first methane oxidation product in the ruminant exhalation after oxidizing the methane in the ruminant exhalation, wherein the first methane oxidation product may be different from the second methane oxidation product.

Figure 6:
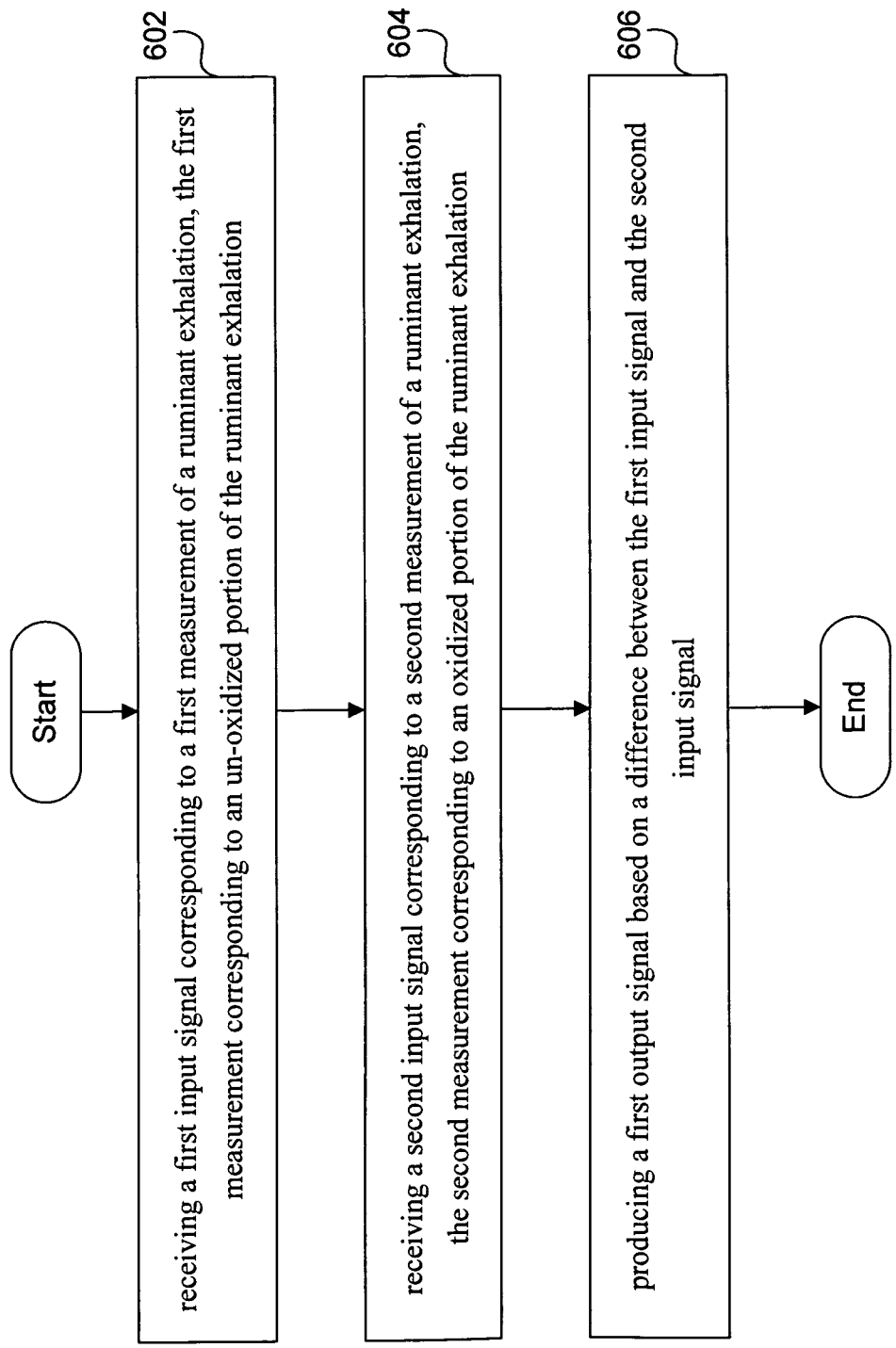

In one embodiment, depicted in the flow chart of FIG. 6, a method comprises (602) receiving a first input signal corresponding to a first measurement of a ruminant exhalation, the first measurement corresponding to an un-oxidized portion of the ruminant exhalation, (604) receiving a second input signal corresponding to a second measurement of a ruminant exhalation, the second measurement corresponding to an oxidized portion of the ruminant exhalation, and (606) producing a first output signal based on a difference between the first input signal and the second input signal. The method may be performed, for example, with the circuitry 402 as shown and described with respect to FIG. 4. The first and/or second measurements of a ruminant exhalation may correspond to first and/or second detected levels of the ruminant exhalation. For example, the "measurement" may not determine an absolute quantity but may simply correspond to a detected level, which may be compared with other detected levels obtained in a similar way.

In some embodiments producing a first output signal based on a difference between the first input signal and the second input signal may include determining an amount of methane oxidized during the oxidation of the exhalation, wherein the output signal may include information related to the determined amount of methane oxidized during the oxidation of the exhalation. In some embodiments producing a first output signal based on a difference between the first input signal and the second input signal may include determining an amount of a methane oxidation product produced during the oxidation of the exhalation, wherein producing a first output signal based on a difference between the first input signal and the second input signal may further include determining a net environmental offset corresponding to the amount of methane oxidized and the amount of the methane oxidation product produced. The method may further comprise associating a monetary value to the determined net environmental offset.

Figure 7:
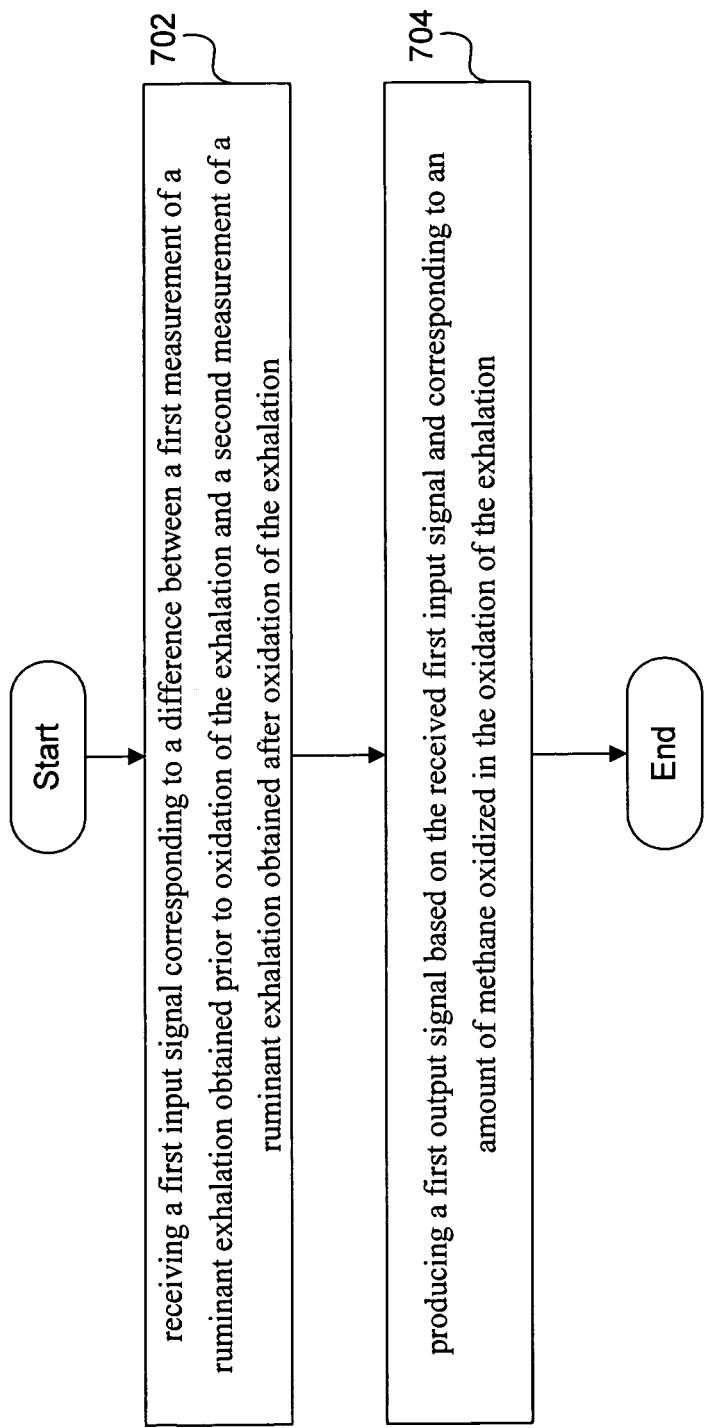

In one embodiment, depicted in the flow chart of FIG. 7, a method comprises (702) receiving a first input signal corresponding to a difference between a first measurement of a ruminant exhalation obtained prior to oxidation of the exhalation and a second measurement of a ruminant exhalation obtained after oxidation of the exhalation, and (704) producing a first output signal based on the received first input signal and corresponding to an amount of methane oxidized in the oxidation of the exhalation. In some embodiments, the first input signal may correspond to an on state, and the method may further comprise receiving a second input signal corresponding to a difference between a third measurement of a ruminant exhalation obtained prior to oxidation of the exhalation and a fourth measurement of a ruminant exhalation obtained after oxidation of the exhalation, the second input, signal corresponding to an off state. Producing a first output signal may further include producing the first output signal based on the received first signal and the received second signal.

In some embodiments, the first input signal may correspond to a first ruminant, and the method may further comprise receiving a second input signal corresponding to a difference between a third measurement of a ruminant exhalation obtained prior to oxidation of the exhalation and a fourth measurement of a ruminant exhalation obtained after oxidation of the exhalation, the second input signal corresponding to a second ruminant different from the first ruminant. The method may further comprise producing a second output signal based on the received second input signal.

In some embodiments the method may further comprise receiving a second input signal corresponding to a difference between a third measurement of a ruminant exhalation obtained prior to oxidation of the exhalation and a fourth measurement of a ruminant exhalation obtained after oxidation of the exhalation, wherein the first input signal corresponds to a first time and the second input signal corresponds to a second time different from the first time, and producing the first output signal based on the received first and second input signals and corresponding to an amount of methane oxidized, and further corresponding to a time difference between the first time and the second time.

Figure 8:
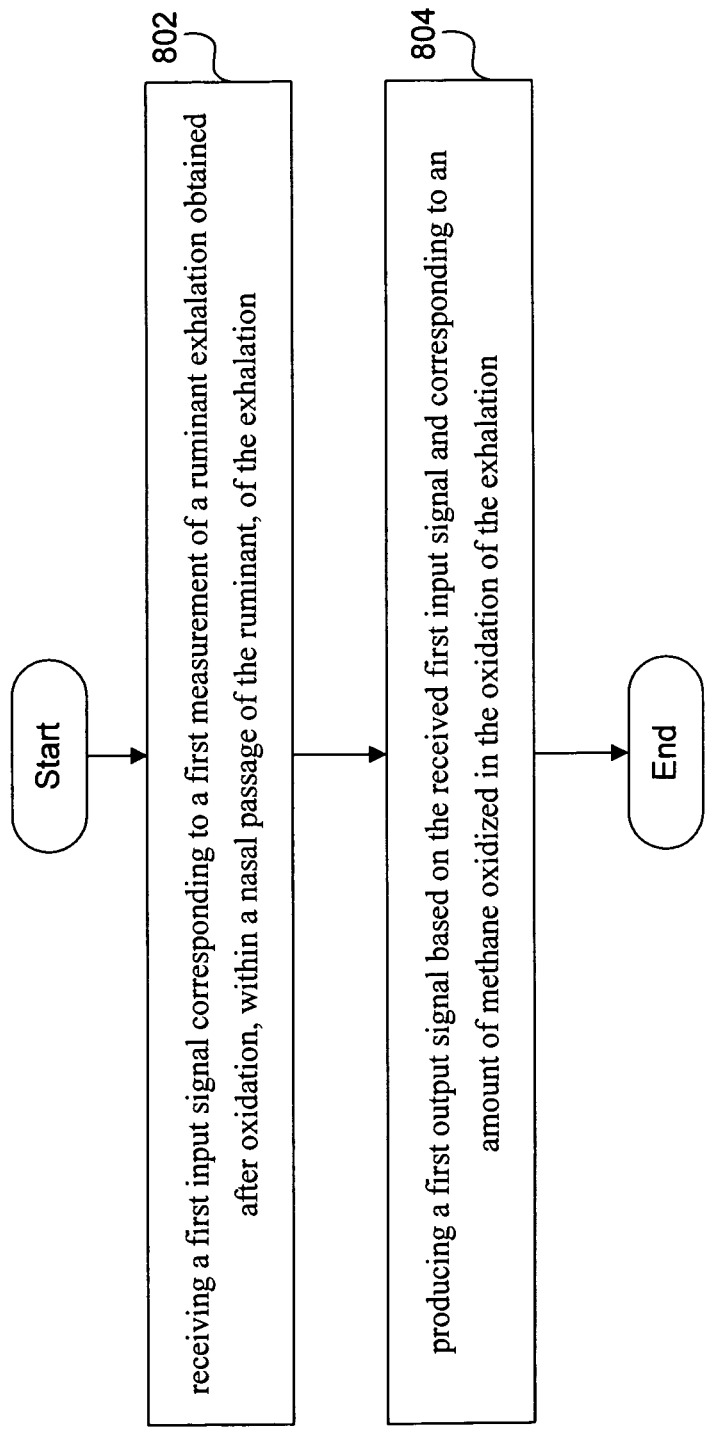

In one embodiment, depicted in the flow chart of FIG. 8, a method comprises (802) receiving a first input signal corresponding to a first measurement of a ruminant exhalation obtained after oxidation, within a nasal passage of the ruminant, of the exhalation, and (804) producing a first output signal based on the received first input signal and corresponding to an amount of methane oxidized in the oxidation of the exhalation.

Figure 9:
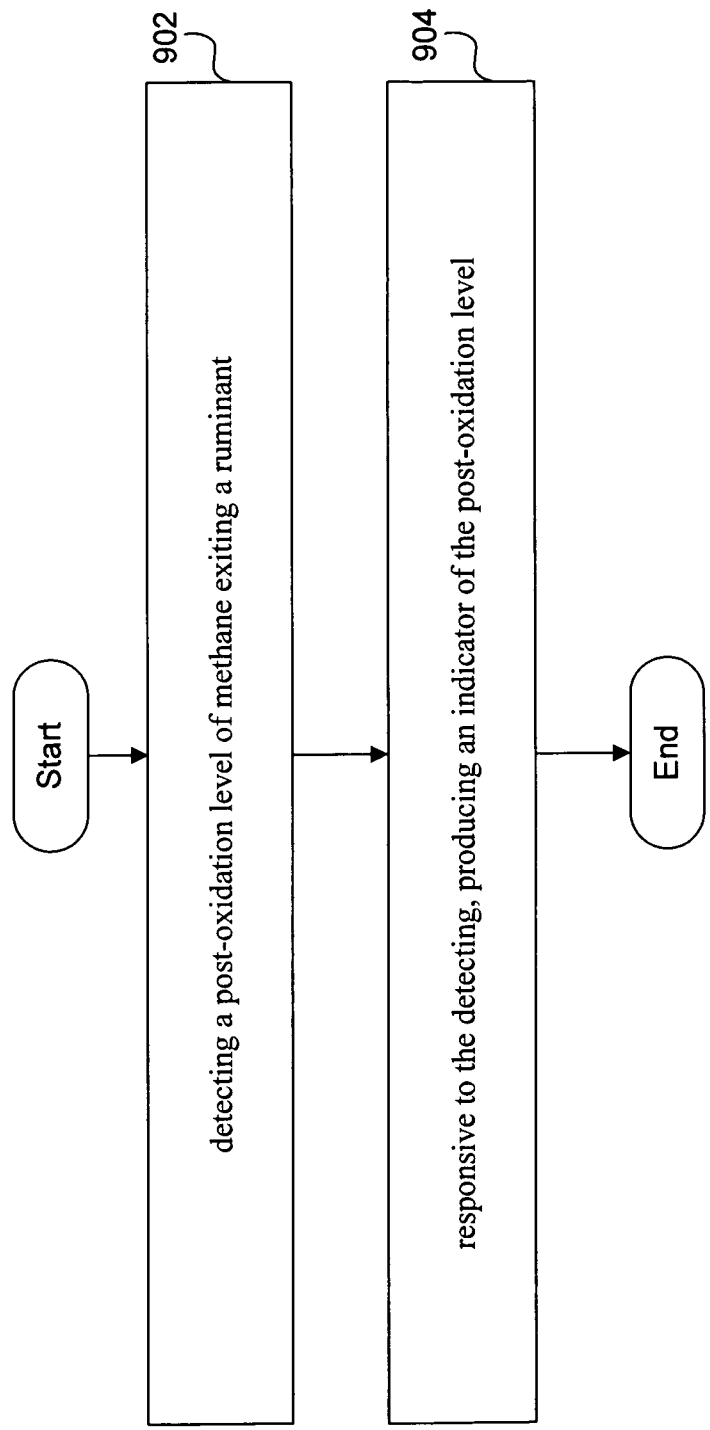

In one embodiment, depicted in the flow chart of FIG. 9, a method comprises (902) detecting a post-oxidation level of methane exiting a ruminant, and (904) responsive to the detecting, producing an indicator of the post-oxidation level. In some embodiments, the indicator may include a visible indicia of an accepted level, an electromagnetic signal, and/or a different indicator.

Each of the method as described herein may be performed with one or more other methods described herein and/or one or more methods for using the apparatus as described with respect to FIGS. 1-4. Further, many of the methods as described herein, including methods for using the apparatus as described with respect to FIGS. 1-4, may be followed by sending a signal corresponding to one or more results obtained in executing the method.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit a device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems.

Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/ or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Those skilled in the art will appreciate that "user" may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A ruminant exhalation treatment device suitable for retention in a nasal passage of a ruminant, the device comprising:
a thermally insulating sleeve having an exterior surface contoured to retain the sleeve in the nasal passage of a ruminant, wherein a first exhalation opening at one end of the sleeve is positioned opposite from a second exhalation opening on the other end of the sleeve; and
a first structure configured to oxidize methane gas in the ruminant exhalations being held within the sleeve in a space between the opposite ends of the sleeve, wherein a portion of the ruminant exhalations entering the first exhalation opening and traversing the first structure is oxidized and products of the oxidized methane gas pass through second exhalation opening toward a nasal passage exit of the ruminant.

2. The apparatus of claim 1 wherein the first structure configured to oxidize methane gas further includes: a first substrate; and a first washcoat support in intimate contact with the first substrate, wherein the catalyst is carried by the washcoat support.

3. The apparatus of claim 2 wherein the first substrate forms a substantially honeycomb structure.

4. The apparatus of claim 2 wherein the substrate forms a spiral coil.

5. The apparatus of claim 1 wherein the catalyst includes a noble metal.

6. The apparatus of claim 1 further comprising: a shutter positioned in between the pair of openings and in the nasal exhalation flow path and configured to adjust a flow of nasal exhalation traversing the methane oxidation catalyst.

7. The apparatus of claim 1 further comprising: a first methane detector positioned in the space between the first and second exhalation openings and configured to detect methane gas in the ruminant exhalations.

8. The apparatus of claim 7 wherein the first structure spans less than a full width of the sleeve, and wherein the first methane detector is located to detect methane in a portion of the ruminant exhalation that bypasses the first structure.

9. The apparatus of claim 7 wherein the first structure has an on state and an off state, and wherein the first methane detector is arranged to detect methane when the first structure is in the off state.

10. The apparatus of claim 7 further comprising: a second methane detector positioned in the space between the first and second exhalation openings and configured to detect methane gas in the ruminant exhalations, the second methane detector positioned at a different location in the space from the first methane detector.

11. The apparatus of claim 10 further comprising: circuitry configured to receive a signal from the first and second methane detectors.

12. The apparatus of claim 11 further comprising: a storage medium operably connected to the circuitry.

13. The apparatus of claim 11 further comprising: a transmitter operably connected to the circuitry and configured to send the signals from the first and second methane detectors.

14. The apparatus of claim 11 wherein the circuitry is further configured to determine an amount of methane oxidized based on the received signals from the first and second methane detectors.

15. The apparatus of claim 14 further comprising: a transmitter operably connected to the circuitry, the transmitter being configured to send a first signal corresponding to the determined amount of methane oxidized.

16. The apparatus of claim 15 wherein the device is associated with an identification, and wherein the transmitter is further configured to include the identification in the first signal.

17. The apparatus of claim 15 further comprising: a tracker configured to determine the location of the ruminant, the tracker being operably connected to the transmitter; and wherein the transmitter is further configured to include information from the tracker in the first signal.

18. The apparatus of claim 14 wherein the circuitry is further configured to determine a time interval associated with the amount of methane oxidized.

19. The apparatus of claim 1 further comprising: a first gas detector positioned in the space between the first and second exhalation openings and configured to detect methane oxidation product in the ruminant exhalations.

20. The apparatus of claim 19 wherein the methane oxidation product includes carbon dioxide.

21. The apparatus of claim 1 further comprising: circuitry operably connected to the first structure to control the oxidation of the methane gas.

22. The apparatus of claim 1 further comprising: a flow control device arranged proximate to the first structure and configured to adjust the flow of the ruminant exhalation through the first structure.

23. The apparatus of claim 1 further comprising: a heating element arranged to heat the first structure.

24. The apparatus of claim 23 further comprising: circuitry configured to control the heating element.

25. The apparatus of claim 23 further comprising: a power supply configured to provide power to the heating element.

26. The apparatus of claim 1 further comprising: a heat sensor arranged to measure a temperature proximate to the first structure.

27. The apparatus of claim 1 further comprising: a fan arranged to transfer heat away from the device.

28. The apparatus of claim 1 further comprising: a heat pipe arranged to transfer heat away from the device.

29. The apparatus of claim 1 wherein the device is associated with an identification, and wherein the apparatus further comprises: circuitry operably connected to the device and configured to send a signal including information corresponding to the identification.

30. The apparatus of claim 1 further comprising: a tracker configured to determine a location of the ruminant.

31. The apparatus of claim 30 further comprising: circuitry operably connected to the tracker and configured to send a signal corresponding to the location of the ruminant.

32. The apparatus of claim 1 further comprising: a heat sensor configured to determine a temperature proximate to the first structure; a meter configured to determine an amount of ruminant exhalation proximate to the first structure; and circuitry configured to determine an amount of methane oxidized based on the determined temperature and amount of ruminant exhalation proximate to the first structure.

33. The apparatus of claim 1 further comprising: circuitry configured to determine an amount of methane oxidized by the device and configured to generate an output signal responsive to the determined amount.

34. The apparatus of claim 33 further comprising: a storage medium operably connected to the circuitry, the storage medium being configured to store data corresponding to at least one of an amount of methane detected, an amount of methane oxidation product detected, and a determined amount of methane oxidized.

35. The apparatus of claim 33 further comprising: a transmitter operably connected to the circuitry, the transmitter being configured to send a signal corresponding to at least one of an amount of methane detected, an amount of methane oxidation product detected, and a determined amount of methane oxidized.

36. The apparatus of claim 35 wherein the transmitter is configured to send the signal using at least one of physical data storage media, wireless signal transmission, and a physical signal transmission media.

37. The apparatus of claim 1, wherein the exterior surface includes a moisture-expandable material adapted to conform the exterior surface to a nasal passage contour of the ruminant.

* * * * *